United States Patent [19]

Kesseler et al.

[11] Patent Number: 5,091,386
[45] Date of Patent: Feb. 25, 1992

[54] 7-SUBSTITUTED DERIVATIVES OF 3,5-DIHYDROXYHEPT-6-YNOIC ACIDS AND CORRESPONDING LACTONES AND THEIR USE AS HYPERCHOLESEROLEMICS

[75] Inventors: Kurt Kesseler; Wilhelm Bartmann, both of Soden am Taunus; Günther Wess, Erlensee; Ernold Granzer, Kelkheim, all of Fed. Rep. of Germany

[73] Assignee: Hoechst Aktiengesellschaft, Frankfurt, Fed. Rep. of Germany

[21] Appl. No.: 411,003

[22] Filed: Sep. 22, 1989

[30] Foreign Application Priority Data

Sep. 24, 1988 [DE] Fed. Rep. of Germany ....... 3832570

[51] Int. Cl.$^5$ .................. C07D 213/55; C07D 405/06; A61K 31/44
[52] U.S. Cl. .................................... 514/277; 514/336; 546/268; 546/341
[58] Field of Search ................ 546/268, 341; 514/277, 514/336

[56] References Cited

U.S. PATENT DOCUMENTS

| | | | |
|---|---|---|---|
| 4,647,576 | 3/1987 | Hoefle | 548/517 |
| 4,761,419 | 8/1922 | Picard | 514/314 |
| 4,851,427 | 7/1989 | Wareing | 514/422 |

FOREIGN PATENT DOCUMENTS 0221025  5/1987  European Pat. Off. ............ 549/417

OTHER PUBLICATIONS

Stokker et al., "Hydroxy-3-methylglutaryl-coenzyme A Reductase Inhibitors 3. 5-Disubstituted [1,1'-biphenyl]-2-yl)-3,5-dihydroxy-6-heptenoic Acids and Their Lactone Derivatives", 29 J. Med. Chem., No. 2, 170-181 (1986).

"Eptastatin Sdoium", 12 Drugs of the Future, No. 5, 437-442 (1987).
Baader et al., "Synthesis of a Novel HMG-CoA Reductase Inhibitor", 29 Tetrahedron Letters, No. 8, 929-930 (1988).
Stokker et al., "Hydroxy-3-methylglutaryl-coenzyme A Reductase Inhibitors. 1. Structural Modification of 5-Substituted 3,5-Dihydroxypentanoic Acids and Their Lactone Derivatives", 28 J. Med. Chem., No. 3, 347-358 (1985).

Primary Examiner—Alan L. Rotman
Attorney, Agent, or Firm—Finnegan, Henderson, Farabow, Garrett and Dunner

[57] ABSTRACT

7-Substituted 3,5-dihydroxyhept-6-ynoic acids and the derivatives thereof of the formula I

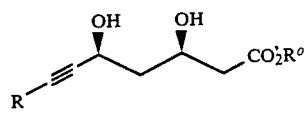

as well as the corresponding lactones of the formula II

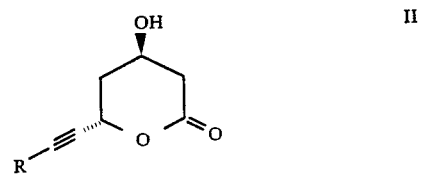

in which R and R° have the specified meanings, a process for the preparation of these compounds, the use thereof as pharmaceuticals and pharmaceutical products are described. In addition, new intermediates for the preparation of the compounds of the formula I or formula II are described.

8 Claims, No Drawings

7-SUBSTITUTED DERIVATIVES OF 3,5-DIHYDROXYHEPT-6-YNOIC ACIDS AND CORRESPONDING LACTONES AND THEIR USE AS HYPERCHOLESEROLEMICS

DESCRIPTION

The conversion of 3-hydroxy-3-methylglutaric acid (HMG) into mevalonic acid forms the key step in the biosynthesis of cholesterol. This step is catalyzed by the enzyme 3-hydroxy-3-methylglutaryl-coenzyme A reductase (HMG-CoA reductase). A large number of compounds which inhibit the activity of HMG-CoA reductase have been described. In most cases these are derivatives of 3,5-dihydroxyheptanoic acid and 3,5-dihydroxyhept-6E-enoic acid, as well as derivatives of 3,5-dihydroxy-6-oxohexanoic acid (cf., for example, Drugs of the Future 12, 437 (1987)), which are substituted in position 7 or on the oxygen atom by sterically demanding lipophilic radicals. Examples of suitable lipophilic part-structures which have been described are hexahydronaphthyl radicals, as in the natural substances compactin (cf. A.G. Brown et al., J. Chem. Soc. Perkin Trans 1, 15 1976, 1165) and mevinolin (cf. A. W. Alberts et al., Proc. Natl. Sci. U.S.A. 77, 3957 (1980)), substituted phenyl nuclei (cf., for example, G. E. Stokker et al., J. Med. Chem. 29, 170 (1986)), heteroaromatic radicals (cf., for example, Drugs of the Future 12, 437 (1987), EP-A 0,221,025), or else triply substituted ethylene groups (cf, for example, E. Baader et al., Tetrahedron Lett, 29, 929 (1988)).

The degree and pattern of the substitution of the said lipophilic radicals are of crucial importance for the biological activity of the HMG-CoA reductase inhibitors. Values for the enzyme inhibition of $IC_{50} \leq 1 \times 10^{-8}$ mol/liter can be reached by suitable substitution of the lipophilic radicals.

Only very little has been published about 7-substituted 3,5-dihydroxyhept-6-ynoic acid derivatives and their inhibitory effect on HMG-CoA reductase. To our knowledge only a single example of a 7-phenyl-substituted derivative is mentioned in the literature (G. E. Stokker et al., J. Med. Chem. 28, 346 (1985)). However, the enzyme inhibition by this compound is weak ($IC_{50} >> 1 \times 10^{-6}$ mol/liter) and, moreover, distinctly less than that of the identically substituted 3,5-dihydroxyheptanoic and 3,5-dihydroxyhept-6E-enoic acid.

In contrast to these results, it has been found that derivatives of 3,5-dihydroxyhept-6-ynoic acid of the general formulae I and II
a) are potent inhibitors of HMG-CoA reductase ($IC_{50} \leq 1 \times 10^{-8}$ mol/liter) and
b) have an inhibitory effect which is equal to or larger than that of the corresponding, i.e. identically substituted on position 7, derivatives of 3,5-dihydroxyhept-6E-enoic acid.

Hence the invention relates to 7-substituted 3,5-dihydroxyhept-6-ynoic acids and the derivatives thereof of the formula I

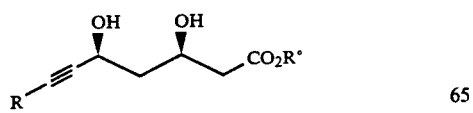

as well as the corresponding lactones of the formula II

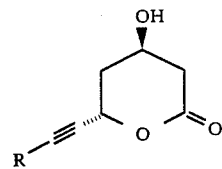

In the formulae I and II, R denotes
a) a radical of the formula a

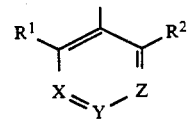

in which
$R^1$ and $R^2$ are, independently of one another, a straight-chain or branched alkyl or alkenyl radical having up to 6 carbon atoms, a saturated or up to doubly unsaturated cyclic hydrocarbon radical having 3–6 carbon atoms or a phenyl radical which is optionally substituted by 1–3 identical or different radicals selected from the group comprising straight-chain or branched alkyl having up to 4 carbon atoms, halogen, alkoxy having up to 4 carbon atoms and hydroxyl, and
X=Y—Z is a group of the formula $CR^3=CR^4—CR^5$, $N=CR^4—CR^5$, $N=N—CR^5$, $N=CR^4—N$, in which
$R^3$, $R^4$, $R^5$ are, independently of one another, hydrogen, a straight-chain or branched alkyl or alkenyl radical having up to 6 carbon atoms, a saturated or up to doubly unsaturated cyclic hydrocarbon radical having 3–6 carbon atoms or a phenyl radical which is optionally substituted by 1–3 identical or different radicals selected from the group comprising straight-chain or branched alkyl having up to 4 carbon atoms, halogen, alkoxy having up to 4 carbon atoms and hydroxyl,
b) a radical of the formula b

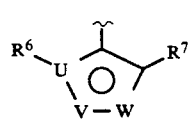

in which
$R^6$ and $R^7$ are, independently of one another, a straight-chain or branched alkyl or alkenyl radical having up to 6 carbon atoms, a saturated or up to doubly unsaturated cyclic hydrocarbon radical having 3–6 carbon atoms, a phenyl radical which is optionally substituted by 1–3 identical or different radicals selected from the group comprising straight-chain or branched alkyl having up to 4 carbon atoms, halogen and alkoxy having up to 4 carbon atoms, and U-V-W is a group of the formula $C—NR^9—CR^8$, $C—O—CR^8$, $C—S—CR^8$, $C—NR^9—N$, $C—O—N$ (=C—N—O), $C—S—N$ (=C—N—S), $N—CR^{10}=CR^8$, $N—N=CR^8$ or $N—CR^{10}=N$, in which $R^8$ is hydrogen, a straight-chain or branched alkyl or alkenyl radical having up to 6 carbon atoms, a saturated or up to doubly unsaturated cyclic hydrocarbon radical having 3–6 carbon atoms or a phenyl radical which is optionally substituted by 1–3 identical or different radicals selected from the group comprising straight-chain or branched alkyl having up to 4 carbon atoms, halogen, alkoxy having 1–4 carbon atoms and hydroxyl, and $R^9$, $R^{10}$ are, independently of one another, a straight-chain or branched alkyl or alkenyl radical having up to 6 carbon atgoms, a saturated or up to doubly unsaturated cyclic hydrocarbon radical having 3–6 carbon atoms or a phenyl radical which is optionally substituted by 1–3 identical or different radicals selected from the group comprising straight-chain or branched alkyl having up to 4 carbon atoms, halogen and alkoxy having up to 4 carbon atoms, or c) a radical of the formula c

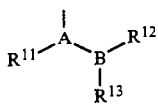

in which

A—B is a group of the formula CH—CH or C=C, and $R^{11}$, $R^{12}$, $R^{13}$ are, independently of one another, a straight-chain or branched alkyl or alkenyl radical having up to 20 carbon atoms, a saturated or up to doubly unsaturated cyclic hydrocarbon radical having 3–6 carbon atoms or a phenyl radical which is optionally substituted by 1–3 radicals selected from the group comprising straight-chain or branched alkyl having up to 4 carbon atoms, halogen, alkoxy having up to 4 carbon atoms and hydroxyl, and $R^0$ denotes hydrogen, a straight-chain or branched alkyl radical having up to 6 carbon atoms, alkali metal or ammonium.

Preferred among the substituents R are:
a) a radical of the formula a in which
  $R^1$ is a straight-chain or branched alkyl radical having up to 4 carbon atoms or a cycloalkyl radical having 3–6 carbon atoms,
  $R^2$ is a phenyl radical which is optionally substituted by 1–3 identical or different radicals selected from the group comprising C1–C4-alkyl, fluorine, chlorine, alkoxy having 1–4 carbon atoms and hydroxyl, and X=Y—Z is a group of the formula CR$^3$=CR$^4$—CR$^5$, N=CR$^4$—CR$^5$, N=N—CR$^5$ or N=CR$^4$—N, in which
  $R^3$, $R^5$ are, independently of one another, hydrogen, a straight-chain or branched alkyl radical having up to 4 carbon atoms, a cycloalkyl radical having 3–6 carbon atoms or a phenyl radical which is optionally substituted by 1–3 identical or different radicals selected from the group comprising C1–C4-alkyl, fluorine, chlorine, alkoxy having 1–4 carbon atoms and hydroxyl, and
  $R^4$ is a straight-chain or branched alkyl radical having up to 4 carbon atoms, a cycloalkyl radical having 3–6 carbon atoms, or a phenyl radical which is optionally substituted by 1–3 identical or different radicals selected from the group comprising C1–C4-alkyl, fluorine, chlorine, alkoxy having 1–4 carbon atoms and hydroxyl, b) a radical of the formula b in which
  $R^6$ is a straight-chain or branched alkyl radical having up to 4 carbon atoms, a cycloalkyl radical having 3–6 carbon atoms,
  $R^7$ is a phenyl radical which is optionally substituted by 1–3 identical or different radicals selected from the group comprising C1–C4-alkyl, fluorine, chlorine, alkoxy having 1–4 carbon atoms and hydroxyl, and
  U—V—W is a group of the formula C—NR$^9$—CR$^8$ in which
    $R^8$ is hydrogen, a straight-chain or branched alkyl radical having up to 4 carbon atoms, a cycloalkyl radical having 3–6 carbon atoms, or a phenyl radical which is optionally substituted by 1–3 identical or different radicals selected from the group comprising C1–C4-alkyl, fluorine and chlorine, and
    $R^9$ is a straight-chain or branched alkyl radical having up to 4 carbon atoms, a cycloalkyl radical having 3–6 carbon atoms or a phenyl radical which is optionally substituted by 1–3 identical or different radicals selected from the group comprising C1–C4-alkyl, fluorine and chlorine, c) a radical of the formula c in which
  A—B is a group of the formula CH—CH or C=C,
  $R^{11}$ is a straight-chain or branched alkyl radical having up to 6 carbon atoms, a cycloalkyl radical having 3–6 carbon atoms, and
  $R^{12}$, $R^{13}$ are, independently of one another, a straight-chain or branched alkyl radical having up to 6 carbon atoms, a cycloalkyl radical having 3–6 carbon atoms, a phenyl radical which is optionally substituted by 1–3 identical or different radicals selected from the group comprising C1–C4-alkyl, halogen, alkoxy having 1–4 carbon atoms and hydroxyl.

Preferred among the radicals $R^0$ are hydrogen, a straight-chain or branched alkyl radical having up to 4 carbon atoms, sodium, potassium.

Particularly preferred among the radicals R are:
a) a radical of the formula a in which
  X=Y—Z is a group of the formula CR$^3$=CR$^4$—CR$^5$ in which
    $R^3$ denotes hydrogen,
    $R^4$ denotes isopropyl, tert.-butyl, phenyl or 4-fluorophenyl, and
    $R^5$ denotes hydrogen, and
    $R^1$ is isopropyl and
    $R^2$ is 4-fluorophenyl,
  X=Y—Z is a group of the formula N=CR$^4$—CR$^5$ in which
    $R^4$ denotes isopropyl, tert.-butyl, phenyl or 4-fluorophenyl and
    $R^5$ denotes hydrogen, and
    $R^1$ is isopropyl or cyclopropyl and
    $R^2$ is 4-fluorophenyl,
  X=Y—Z is a group of the formula N=N—CR$^5$ in which
    $R^5$ denotes phenyl, 4-fluorophenyl, and
    $R^1$ is isopropyl and
    $R^2$ is 4-fluorophenyl,
  X=Y—Z is a group of the formula N=CR$^4$—N in which $R^4$ denotes isopropyl, tert.-butyl, phenyl or 4-fluorophenyl, and
$R^1$ is isopropyl and
$R^2$ is fluorophenyl,
b) a radical of the formula b in which
$R^6$ is isopropyl
$R^7$ is 4-fluorophenyl, and
U—V—W is a group of the formula C—NR$^9$—CR$^8$ in which
$R^8$ denotes hydrogen
$R^9$ denotes isopropyl or phenyl,
c) a radical of the formula c in which
A—B is a group of the formula C=C,
$R^{11}$ is isopropyl and
$R^{12}$=$R^{13}$ are 4-fluorophenyl or 4-fluoro-3-methylphenyl.

Particularly preferred among the radicals $R^0$ are hydrogen, methyl, ethyl, tert.-butyl, sodium and potassium.

The invention relates to the pure enantiomers as well as the racemates of the formula I and mixtures thereof, that is to say the racemates with the absolute configuration 3RS/5RS, as well as the pure enantiomers with the absolute configuration 3R/5S.

The invention furthermore relates to the pure enantiomers as well as the racemates of the general formula II derived from the abovementioned stereoisomeric dihydroxycarboxylic acid derivatives of the general formula I. Specifically, these are the racemates with the absolute configuration 4RS/6SR and the pure enantiomers with the absolute configuration 4R/6S.

The invention further relates to a process for the preparation of the compounds of the general formulae I and II, which comprises
a) converting aldehydes of the formula III

in which R has the specified meaning, into the corresponding hydroxy keto esters of the general formula IV

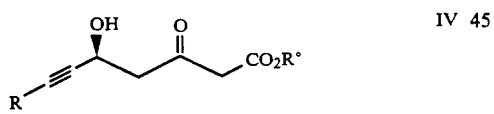

in which R has the specified meaning, and $R^0$ denotes alkyl having 1-6 carbon atoms,
b) converting the hydroxy keto esters of the formula IV into the corresponding 3,5-dihydroxy compounds of the formula I

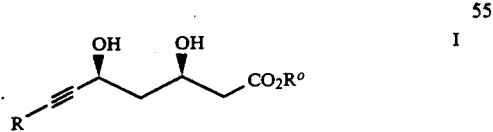

in which R has the meaning specified for formula I, and $R^0$ is alkyl having 1 to 6 carbon atoms, and, where appropriate, hydrolyzing a resulting compound to a compound of the formula I in which $R^0$ represents an alkali metal, liberating therefrom where appropriate the free acid ($R^0$=hydrogen), and converting the free acid where appropriate into a compound of the formula I in which $R^0$ has the meanings specified for formula I with the exception of hydrogen,
c) and converting a resulting compound of the general formula I where appropriate into a lactone of the formula II

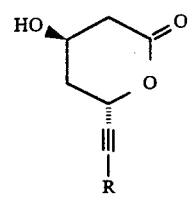

in which R has the specified meaning.

Examples of different variants for the conversion of compounds of the formula III into compounds of the formula IV depending on the circumstances and requirements are:

1. Reaction of the dianion of acetoacetic esters with aldehydes of the formula III in solvents such as THF at −78° C. to room temperature leads to racemic compounds of the formula IV. Dianions of acetoacetic esters can be prepared with various bases, preferably sodium hydride, n-butyllithium and lithium diisopropylamide (LDA) in ethereal solvents, preferably in diethyl ether, THF or dimethoxyethane, at −40° C. to room temperature.

2. Reaction of enolates of non-chiral acetic esters, such as, for example, the methyl, ethyl or propyl ester, which are prepared with strong bases such as, for example, metal amides, preferably LDA, in ethereal solvents, for example THF, with aldehydes of the formula III in solvents such as, for example, THF at temperatures between −78° C. leads to racemic compounds of the formula V

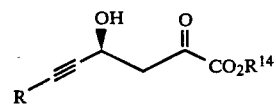

in which $R^{14}$ denotes a non-chiral acid protective group such as, for example, the methyl, ethyl or propyl group. Reaction with another acetic ester enolate in solvents such as, for example, THF at temperatures from −78° C. to 30° C. leads to racemic compounds of the formula IV.

3. Reaction of aldehydes of the formula III with enolates of optically active acetic esters, preferably lithium or magnesium enolates, in solvents such as, for example, THF at temperatures from −78° C. to 0° C. leads to optically active adducts of the formula V. In this case $R^{14}$ denotes a suitable optically active acid protective group which determines the configuration at C-3. Preferably used in this case is the group

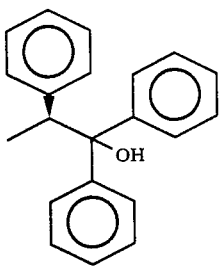

which, according to R. Devant, U. Mahler and M. Braun (Chem. Ber. 121, 397 (1988)) yields the 3R configuration and is prepared from L-(+)-mandelic acid. However, other optically active groups are also suitable. The resulting optically active compounds of the formula V are either directly reacted with non-chiral acetic ester enolates to give optically active compounds of the formula IV or initially converted by transesterification into alkyl esters of the formula V, preferably methyl esters, which are then converted by variant 2 into compounds of the formula IV.

The conversion of compounds of the formula IV into compounds of the formula I is carried out in analogy to processes known from the literature (see, for example, K. Naraska, H. C. Pai, Chem. Lett. 1980, 1415 or K. M. Chen, K. G. Gunderson, G. E. Hardtmann, K. Prasad, O. Repic and M. J. Shapiro, Chem. Lett. 1978, 1923). A compound of the formula IV is first reacted with a trialkyl- or alkoxydialkylborane, preferably triethyl- or methoxydiethylborane, and then reduced at $-78°$ C. to $0°$ C., where appropriate with the addition of methanol. Compounds of the formula I with the specified relative configuration at C-3 and C-5 (3R*, 5S*) are obtained in this way.

The salts and acids of compounds of the general formula I are obtained by generally known methods.

Lactones of the general formula II are likewise obtained by processes known per se, for example by elimination of water from the dihydroxy carboxylic acids of the formula I ($R^0$=H) in benzene, hexane or toluene with the addition of p-toluenesulfonic acid at room temperature to the reflux temperature, or else from dihydroxy carboxylic esters of the formula I, for example $R^0$=methyl, ethyl, tert.-butyl, in dichloromethane with the addition of strong acids, such as, for example, trifluoroacetic acid at room temperature to the reflux temperature.

The racemic compounds of the formulae I and II can be separated into the pure enantiomers by the known processes of racemate resolution.

The aldehydes III in which R has the meaning given for the general formula I and which are used as starting material in the process according to the invention are obtained as depicted in scheme 1, for example. Suitable aldehydes of the general formula VI in which R has the meaning specified for formula I are either known from the literature or can be prepared in analogy to the methods described in the literature:

Aldehydes VI with radicals R of the formula a, X=Y—Z =CR$^3$=CR$^4$—CR$^5$: G. E. Stokker et al., J. Med. Chem. 29, 170 (1986)

aldehydes VI with radicals R of the formula a, X=Y—Z =N=CR$^4$—CR$^5$, N=CR$^4$—N: German Offenlegungsschrift 38 23 045 (corresponding to EP-A 0,307,342;

U.S. patent application Ser. No. 07/216,458) (corresponding alcohols R-CH$_2$OH are described, from which aldehydes of the formula III can be prepared by oxidation by known methods, for example with pyridinium chlorochromate)

aldehydes VI with radicals R of the formula a, X=Y—Z =N=N—CR$^5$: German Patent Application P 38 00 785.1 (corresponding to U.S. patent application Ser. No. 07/294,096)

aldehydes VI with radicals R of the formula b, U—V—W =C—NR$^9$—CR$^8$: German Offenlegungsschrift 37 22 806 (corresponding to EP-A 0,300,249; U.S. patent application Ser. No. 216,423)

aldehydes VI with radicals R of the formula b, U—V—W =C—O—CR$^8$, C—S—CR$^8$, N—CR$^{10}$=CR$^8$: EP-A 0,221,025 aldehydes VI with radicals R of the formula b, U—V—W =C—NR$^9$—N, N—N=CR$^8$: WO 86/00307 aldehydes VI with radicals R of the formula b, U—V—W =N—CR$^{10}$=N: WO 86/07054 aldehydes VI with radicals R of the formula b, U—V—W =C—O—N, C—S—N: German Offenlegungsschrift 3,621,372 and literature cited therein (corresponding alcohols R-CH$_2$OH are described, from which the aldehydes of the formula VI are prepared by oxidation by methods known per se)

aldehydes VI with radicals R of the formula c; German Offenlegungsschrift 37 22 807 (corresponding to EP-A 03 06 649; U.S. patent application Ser. No. 07/216,331).

Aldehydes of the formula VI are converted into carboxylic acids of the formula VIII, for example, in analogy to the method described by E. J. Corey and P. L. Fuchs, Tetrahedron Lett. 1972, 3769, by preparation of the corresponding gem-dibromoolefins of the general formula VII and subsequent reaction with n-butyllithium and carbon dioxide.

Carboxylic esters of the formula IX in which $R^{15}$ denotes an alkyl radical, preferably a methyl or ethyl radical, are prepared by esterification by methods known per se. The latter are reduced by known processes, for example by reduction with metal hydrides such as LiAlH$_4$, diisobutylaluminum hydride or Vitride, to alcohols of the formula X. Subsequent oxidation by known processes, for example with pyridinium chlorochromate, leads to the aldehydes of the general formula III.

Scheme 1

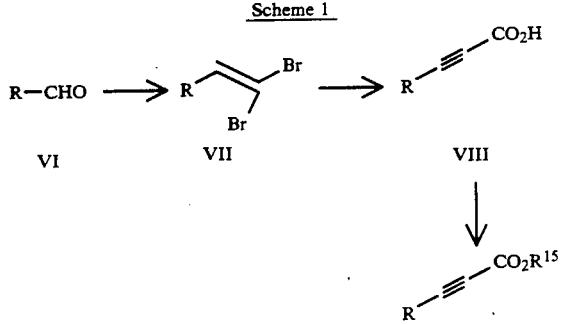

-continued
Scheme 1

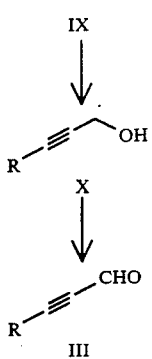

It is expedient for the synthesis of compounds of the general formulae I and II with phenolic hydroxyl groups to protect the latter in a suitable way. Starting from aldehydes of the general formula III with protected phenolic hydroxyl groups, initially compounds of the general formula I or II are prepared, likewise with protected phenolic hydroxyl groups, and the latter are subsequently converted into compounds of the general formula I or II with free phenolic hydroxyl groups. Protective groups suitable for this purpose, such as, for example, alkyl ethers or silyl ethers, as well as suitable processes for the selective introduction and elimination thereof, are generally known (cf., for example, T. W. Greene: Protective Groups in Organic Synthesis, Wiley & Sons, New York 1981).

Besides the compounds described in the examples, the following compounds can be prepared by the process according to the invention:

tert.-butyl 7-(4-(2,2-dimethylethyl)-2-(4-fluorophenyl)-6-(1-methylethyl)phenyl)-3R,5S-dihydroxyhept-6-ynoate tert.butyl 7-(2,4-bis-(4-fluorophenyl)-6-(1-methylethyl)phenyl)-3R,5S-dihydroxyhept-6-ynoate tert.-butyl 7-(6-(2,2-dimethylethyl)-4-(4-fluorophenyl)-2-(1-methylethyl)pyridin-3-yl)-3R,5S-dihydroxyhept-6-ynoate tert.-butyl 7-(2,6-bis-(1-methylethyl)-4-(4-fluorophenyl)pyridin-3-yl)-3R,5S-dihydroxyhept-6-ynoate tert.-butyl 7-(2-cyclopropyl-4-(4-fluorophenyl)-6-(1-methylethyl)pyridin-3-yl)-3R,5S-dihydroxyhept-6-ynoate tert.butyl 7-(2-cyclopropyl-6-(2,2-dimethylethyl)-4-(4-fluorophenyl)pyridin-3-yl)-3R,5S-dihydroxyhept-6-ynoate tert.butyl 7-(4,6-bis-(4-fluorophenyl)-2-cyclopropylpyridin-3-yl)-3R,5S-dihydroxyhept-6-ynoate tert.butyl 7-(4-(4-fluorophenyl)-6-(1-methylethyl)-3-phenylpyridazin-5-yl)-3R,5S-dihydroxyhept-6-ynoate tert.butyl 7-(6-(2,2-dimethylethyl)-4-(4-fluorophenyl)-2-(1-methylethyl)pyrimidin-3-yl)-3R,5S-dihydroxyhept-6-ynoate tert.butyl 7-(4,6-bis-(4-fluorophenyl)-2-(1-methylethyl)pyrimidin-3-yl)-3R,5S-dihydroxyhept-6-ynoate sodium 7-(4-(2,2-dimethyl)-2-(4-fluorophenyl)-6-(1-methylethyl)phenyl)-3R,5S-dihydroxyhept-5-ynoate sodium 7-(2,4-bis-(4-fluorophenyl)-6-(2-methylethyl)phenyl)-3R,5S-dihydroxyhept-6-ynoate sodium 7-(6-(2,2-dimethylethyl-4-(4-fluorophenyl)-2-(1-methylethyl)pyridin-3-yl)-3R,5S-dihydroxyhept-6-ynoate sodium 7-(2,6-bis-(1-methylethyl)-4-(4-fluorophenyl)-pyridin-3-yl)-3R,5S-dihydroxyhept-6-ynoate sodium 7-(2-cyclopropyl-4-(4-fluorophenyl)-6-(1-methylethyl)pyridin-3-yl)-3R,5S-dihydroxyhept-6-ynoate sodium 7-(2-cyclopropyl-6-(2,2-dimethylethyl)-4-(4-fluorophenyl)pyridin-3-yl)-3R,5S-dihydroxyhept-6-ynoate sodium 7-(4,6-bis-(4-fluorophenyl)-2-cyclopropylpyridin-3-yl)-3R,5S-dihydroxyhept-6-ynoate sodium 7-(4-(4-fluorophenyl)-6-(1-methylethyl)-3-phenylpyridazin-5-yl)-3R,5S-dihydroxyhept-6-ynoate sodium 7-(6-(2,2-dimethylethyl)-4-(4-fluorophenyl)-2-(1-methylethyl)pyrimidin-3-yl)-3R,5S-dihydroxyhept-6-ynoate sodium 7-(4,6-bis-(4-fluorophenyl)-2-(1-methylethyl)-pyrimidin-3-yl)-3R,5S-dihydroxyhept-6-ynoate 6S-(2-(4-(2,2-dimethylethyl)-2-(4-fluorophenyl)-6-(1-methylethyl)phenyl)ethynyl-4R-hydroxy-3,4,5,6-tetrahydro-2H-pyran-2-one 6S-(2-(2,4-bis-(4-fluorophenyl)-6-(1-methylethyl)phenyl)ethynyl)-4R-hydroxy-3,4,5,6-tetrahydro-2H-pyran-2-one 6S-(2-(6-(2,2-dimethylethyl)-4-(4-fluorophenyl)-2-(1-methylethyl)pyridin-3-yl)ethynyl)-4R-hydroxy-3,4,5,6-tetrahydro-2H-pyran-2-one 6S-(2-(2,6-bis-(1-methylethyl)-4-(4-fluorophenyl)pyridin-3-yl)ethynyl)-4R-hydroxy-3,4,5,6-tetrahydro-2H-pyran-2-one 6S-(2-(2-cyclopropyl-4-(4-fluorophenyl-6-(1-methylethyl)pyridin-3-yl)ethynyl)-4R-hydroxy-3,4,5,6-tetrahydro-2H-pyran-2-one 6S-(2-(2-cyclopropyl-6-(2,2-dimethylethyl)-4-(4-fluorophenyl)pyridin-3-yl)ethynyl)-4R-hydroxy-3,4,5,6-tetrahydro-2H-pyran-2-one 6S-(2-(4,6-bis-(4-fluorophenyl)-2-cyclopropylpyridin-3-yl)ethynyl)-4R-hydroxy-3,4,5,6-tetrahydro-2H-pyran-2-one 6S-(2-(4-fluorophenyl)-6-(1-methylethyl)-3-phenyl-pyridazin-5-yl)ethynyl)-4R-hydroxy-3,4,5,6-tetrahydro-2H-pyran-2-one 6S-(2-(6-(2,2-dimethylethyl)-4-(4-fluorophenyl)-2-(1-methylethyl)pyridin-3-yl)ethynyl)-4R-hydroxy-3,4,5,6-tetrahydro-2H-pyran-2-one 6S-(2-(4,6-bis-(4-fluorophenyl)-2-(1-methylethyl)-pyrimidin-3-yl)ethynyl)-4R-hydroxy-3,4,5,6-tetrahydro-2H-pyran2-one

BIOLOGICAL TEST SYSTEMS

1. HMG-CoA reductase activity in enzyme preparations

The HMG-CoA reductase activity was measured on solubilized enzyme preparations from liver microsomes of rats which had been induced with cholestyramine (®Cuemid) after changing the day/night rhythm. (Sm R) $^{14}$C-HMG-CoA was used as substrate, and the concentration of NADPH was maintained during the incubation by a regenerating system. $^{14}$C-mevalonate was separated from the substrate and other products (for example $^{14}$C-HMG) by column elution, with the elution profile of each individual sample being determined. $^3$H-Mevalonate was not always included because the object was to determine relative data on the inhibitory effect. In each test series the enzyme-free control, the enzyme-containing normal mixture (=100%) and those with added product, final concentration $10^{-5}$ to $10^{-9}$M, were treated together. Each individual value was formed as the mean of 3 parallel samples. The significance of the differences between means for product-free and product-containing samples was assessed by the t test.

Using the method described above, for example, the following values for the inhibition of HMG-CoA reductase were found for the compounds according to the invention [$IC_{50}$/mol/liter denotes the molar concentration of the compound per liter required for a 50% inhibition].

The $IC_{50}$ values obtained in this way for compounds of the general formula I were compared with those obtained ($IC_{50}$ref.) for the enzyme inhibition by the identically substituted 3,5-dihydroxyhept-6E-enoic acid derivatives (ref. compound). The quotient $IC_{50}$ref./$IC_{50}$ yields the relative activity.

The specific values obtained were those listed in Table I, for example concentrations of the test substances for a defined time (for example 1 hour) and, after addition of the labeled precursor, for example sodium $^{14}$C-acetate, the incubation was continued (for example for 3 hours). After addition of an internal standard ($^3$H-cholesterol) a portion of the cells was subjected to alkaline hydrolysis. The lipids from the hydrolyzed cells were extracted with chloroform/methanol. This lipid mixture was, after addition of carrier cholesterol, subjected to preparative thin-layer chromatography, the cholesterol band was visualized with iodine vapor and then isolated, and the amount of $^{14}$C-cholesterol formed from the $^{14}$C-precursor was determined by scintigraphy. Cell protein was determined in an aliquot of the cells so that it is possible to calculate the amount of $^{14}$C-cholesterol formed in unit time per mg of cell protein. The inhibitory effect of the particular test product on cholesterol biosynthesis by HEP-G2 cell cultures emerged by comparison of this figure with the amount of $^{14}$C-cholesterol

TABLE I

| Compounds according to Example | R | R° | $IC_{50}$/ mol/L | Ref. compound | Relative activity: $IC_{50}$ Ref: $IC_{50}$ |
|---|---|---|---|---|---|
| 7a | a; X=Y—Z:N = CR$^4$CR$^5$, R$^1$ = iC$_3$H$_7$, R$^2$ = 4-FC$_6$H$_4$, R$^4$ = C$_6$H$_5$, R$_5$ = H | Na | $3.0 \times 10^{-9}$ | (German Offen-legungsschrift 38 23 045) | 0.97 |
| 71 | c, R$^{11}$ = iC$_3$H$_7$, R$^{12}$ = R$^{13}$ = 4-FC$_6$H$_4$ A—B = C≡C | Na | $5.7 \times 10^{-9}$ | (Tetrahedron Lett. 29, 929 (1988)) | 1.75 |

2. Suppression or inhibition of HMG-CoA reductase in cell cultures of HEP-G2 cells Monolayers of HEP-G2 cells in lipoprotein-free nutrient medium were preincubated with the appropriate formed per mg of cell protein and unit time in a culture treated in the same way but free of test substance.

Testing of substances for inhibition of cholesterol biosynthesis in confluent cell cultures (monolayers) of HEP-G2 cells

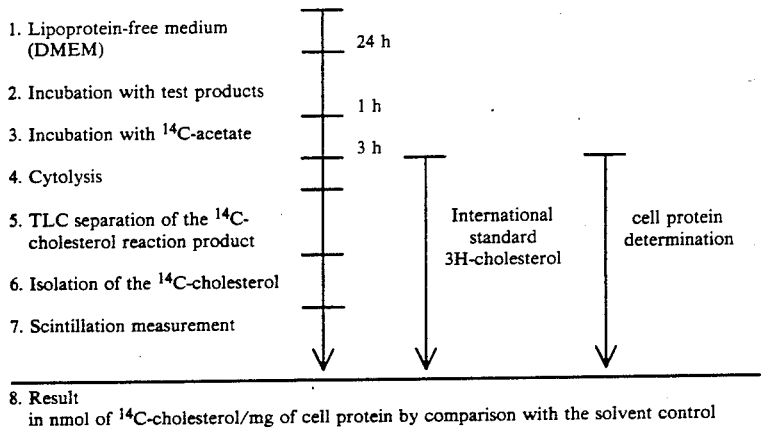

1. Lipoprotein-free medium (DMEM) — 24 h
2. Incubation with test products — 1 h
3. Incubation with $^{14}C$-acetate — 3 h
4. Cytolysis
5. TLC separation of the $^{14}C$-cholesterol reaction product — International standard 3H-cholesterol — cell protein determination
6. Isolation of the $^{14}C$-cholesterol
7. Scintillation measurement
8. Result in nmol of $^{14}C$-cholesterol/mg of cell protein by comparison with the solvent control Using the method described above, for example the following figures for the inhibition of cholesterol biosynthesis (in HEP-G2 cells) were found for the compounds according to the invention (the $IC_{50}$/mol is that concentration of the compound which brings about 50% inhibition of cholesterol biosynthesis). $IC_{50}$ values were determined for the compounds according to the invention as well as for identically substituted 3,5-dihydroxyhept6E-enoic acid derivatives ($IC_{50}$ ref.). The quotient $IC_{50}$ ref./$IC_{50}$ yielded the relative activity of the compounds according to the invention. Thus, for example, for the compound of Example 8 a (R=a; X=Y—Z=N=CR$^4$—CR$^5$, R$^1$=iC$_3$H$_7$, R$^2$=4—FC$_6$H$_4$, R$^4$=C$_6$H$_5$, R$^5$=H) an $IC_{50}$ of $9 \times 10^{-9}$ mol/L was determined, as was a relative activity of 2.67, based on the analogous hept-6E-enoic acid derivative (compare Table I, ref. compound/German Offenlegungsschrift 38 23 045, Example 11 e). The compound of Example 8e (R=a; X=Y—Z=N=CR$^4$—N; R$^1$=iC$_3$H$_7$, R$^2$=4—FC$_6$H$_4$, R$^4$=4—C$_6$H$_4$) inhibits cholesterol biosynthesis with an $IC_{50}$ of $1.1 \times 10^{-8}$ mol/l. This corresponds to a relative activity of 1.6 based on the analogous hept-6E-enoic acid derivative.

The compounds of the general formula I and II are distinguished by potent inhibition of HMG-CoA reductase, the rate-determining enzyme of cholesterol biosynthesis.

The enzyme HMG-CoA reductase is widespread in nature. It catalyzes the formation of mevalonic acid from HMG-CoA. This reaction is a central step in cholesterol biosynthesis (cf. J. R. Sabine in CRC Series in Enzyme Biology: 3-hydroxy-3-methylglutaryl-coenzyme A reductase, CRC Press Inc., Boca Raten, Fla. 1983 (ISBN 0-849-36551-1)).

High cholesterol levels are thought to be associated with a number of diseases such as, for example, coronary heart disease or arteriosclerosis. This is why the lowering of elevated cholesterol levels is an aim of therapy for preventing and treating diseases of these types.

One approach to this comprises inhibiting or reducing endogenous cholesterol biosynthesis. Inhibitors of HMG-CoA reductase block cholesterol biosynthesis at an early stage.

Hence compounds of the general formula I and II are suitable as hypolipidemics and for the treatment and prophylaxis of arteriosclerotic changes.

Hence the invention also relates to pharmaceutical products based on these compounds and to the use thereof as pharmaceuticals, in particular as hypolipidemics and for the prophylaxis of arteriosclerotic changes.

Compounds of the formula I and II are used as hypolipidemics or antiarteriosclerotics in oral doses of 3 to 2500 mg, but preferably in the dose range 10-500 mg. These daily doses can if required also be divided into two to four single doses or administered in depot form. The dosage regimen may depend on the type, age, weight, sex and medical condition of the patient.

An additional cholesterol-lowering effect can be achieved by concurrent administration of the compounds according to the invention with substances which bind bile acids, such as, for example, anion exchanger resins. Excretion of bile acids leads to enhanced de novo synthesis and thus to an increased breakdown of cholesterol (cf. M. S. Brown, P. T. Koranen and J. C. Goldstein, Science 212, 628 (1981); M. S. Brown, J. C. Goldstein, Spektrum der Wissenschaft 1985, 1, 96).

The compounds of the formula I or II according to the invention can be used in the form of the δ-lactones, as free acids, in the form of their physiologically acceptable inorganic or organic salts or as esters. Acids and salts or esters can be used in the form of their aqueous solutions or suspensions or else dissolved or suspended in pharmacologically acceptable organic solvents such as monohydric or polyhydric alcohols such as, for example, ethanol, ethylene glycol or glycerol, in triacetin, in alcohol/acetaldehyde diacetal mixtures, oils such as, for example, sunflower oil or fish liver oil, ethers such as, for example, diethylene glycol dimethyl ether, or else polyethers such as, for example, polyethylene glycol, or else in the presence of other pharmacologically acceptable polymeric vehicles such as, for example, polyvinylpyrrolidone or in solid formulations.

Solid presentations which can be administered orally and which can contain the customary auxiliaries are preferred for the compounds of the formula I and II. They are prepared by customary methods.

Particularly suitable formulations for oral use are tablets, coated tablets or capsules. A dosage unit preferably contains 10 to 500 mg of active substance.

The compounds of the formulae III and IV are new and represent valuable intermediates for the preparation of compounds of the formula I. Hence the invention also relates to these compounds and to processes for the preparation thereof.

Preliminary note: NMR spectra were, unless specified otherwise, recorded in CDCl₃ with TMS as internal standard. The following abbreviations are used to classify NMR signals: s=singlet, d=doublet, t=triplet, q=quartet, h=heptet, m=multiplet. Melting points are uncorrected.

6H), 7.5(s, 1H), 8.1(m, 2H). MS: m/e 478, 476, 474 (M⁺+H) $C_{22}H_{18}Br_2FN$.

EXAMPLE 1 b–1 m

The examples in Table 1 were obtained in analogy to Example 1a.

TABLE 1

$$R = \underset{X=Y}{\overset{R^1}{\underset{Z}{\bigwedge}}}\overset{R^2}{\phantom{X}} \qquad R\overset{Br}{\underset{Br}{=}}$$

| Example | X | Y | Z | R¹ | R² | Yield % | MS: m/e = |
|---|---|---|---|---|---|---|---|
| 1b | N | 4-FC₆H₄—C | CH | iC₃H₇ | 4-FC₆H₄ | 79 | 495, 493, 491 (M⁺) $C_{22}H_{17}Br_2F_2N$ |
| 1c | N | C₆H₅—C | CH | cC₃H₇ | 4-FC₆H₄ | 71 | 477, 475, 473 (M⁺) $C_{22}H_{16}Br_2FN$ m.p. 153–155° C. |
| 1d | N | C₆H₅—C | N | iC₃H₇ | 4-FC₆H₄ | 46 | 478, 476, 474 (M⁺) $C_{21}H_{17}Br_2FN_2$ |
| 1e | N | 4-FC₆H₄—C | N | iC₃H₇ | 4-FC₆H₄ | 86 | 496, 494, 492 (M⁺) $C_{21}H_{16}Br_2F_2N_2$ |
| 1f | N | iC₃H₇—C | N | iC₃H₇ | 4-FC₆H₄ | 53 | 444, 442, 440 (M⁺) $C_{18}H_{19}Br_2FN_2$ |
| 1g | CH | C₆H₅—C | CH | iC₃H₇ | 4-FC₆H₄ | 68 | 476, 474, 472 (M⁺) $C_{23}H_{19}Br_2F$ |
| 1h | CH | iC₃H₇—C | CH | iC₃H₇ | 4-FC₆H₄ | 76 | 442, 440, 438 (M⁺) $C_{20}H_{21}Br_2F$ |
| 1i | N | N | 4-FC₆H₄—C | iC₃H₇ | 4-FC₆H₄ | 50 | 478, 476, 474 (M⁺) $C_{21}H_{17}Br_2FN_2$ |

$$R = \underset{V\underset{\phantom{x}}{-}W}{\overset{R^6}{\underset{\phantom{x}}{\bigwedge}}}\overset{R^7}{\phantom{x}} \qquad R\overset{Br}{\underset{Br}{=}}$$

| Example | U | V | W | R⁶ | R⁷ | Yield % | MS: m/e = |
|---|---|---|---|---|---|---|---|
| 1j | C | C₆H₅—N | C—H | iC₃H₇ | 4-FC₆H₄ | 59 | 465, 463, 461 (M⁺) $C_{21}H_{18}Br_2FN$ |
| 1k | C | iC₃H₇—N | C—H | iC₃H₇ | 4-FC₆H₄ | 63 | 431, 429, 427 (M⁺) $C_{18}H_{20}Br_2FN$ |

$$R = A\underset{R^{11}}{\overset{\phantom{x}}{-}}B\overset{R^{12}}{\underset{R^{13}}{\phantom{x}}} \qquad R\overset{Br}{\underset{Br}{=}}$$

| Example | A—B | R¹¹ | R¹² | R¹³ | Yield % | MS: m/e = |
|---|---|---|---|---|---|---|
| 1l | C=C | iC₃H₇ | 4-FC₆H₄ | 4-FC₆H₄ | 58 | 444, 442, 440 (M⁺) $C_{19}H_{16}Br_2F_2$ |
| 1m | C=C | iC₃H₇ | 4-F-3-CH₃C₆H₃ | 4-F-3-CH₃C₆H₃ | 51 | 472, 470, 468 (M⁺) $C_{21}H_{20}F_2Br_2$ |

The following abbreviations are used for substituents:
i=iso, t=tertiary, c=cyclo.

EXAMPLE 1

General procedure for the preparation of compounds of the general formula VII

EXAMPLE 1 a 1,1-Dibromo-2-(4-(4-fluorophenyl)-2-(1-methylethyl)-6-phenylpyridin-3-yl)ethene (R=a; X=Y—Z=N=C(C₆H₅)—CH, R¹=iC₃H₇, R²=4—FC₆H₄)

5.2 g (80 mmol) of activated Zn dust and 21.0 g (80 mmol) of triphenylphosphine were added to a solution of 26.5 g (80 mmol) of carbon tetrabromide in 500 ml of dichloromethane. The suspension was stirred at room temperature for 30 h and then a solution of 12.8 g (40 mmol) of 4-(4-fluorophenyl)-2-(1-methylethyl)-6-phenylpyridine-3-aldehyde in 400 ml of dichloromethane was added. The reaction mixture was refluxed for 48 h and filtered. The solid constituents were washed with 400 ml of dichloromethane, and the filtrates were combined, extracted by shaking with water, dried over MgSO₄ and evaporated. Purification of the residue by chromatography provided 13.0 g (68%) of the title compound.

Melting point: 116°–118° C.; ¹H NMR: δ=1.4(d, J=7 Hz, 6H), 3.2(h, J=7 Hz, 1H), 7.1(m, 2H), 7.3–7.5(m,

EXAMPLE 2

General procedure for the preparation of compounds of the formula IX

EXAMPLE 2a

Methyl 3-(4-(4-fluorophenyl)-2-(1-methylethyl)-6-phenylpyridin-3-yl)prop-2-ynoate (R=a; X=Y—Z=N=C(C₆H₅)—CH, R¹=iC₃H₇, R²=4F—C₆H₄, R¹⁵=CH₃)

A)
3-(4-(4-Fluorophenyl)-2-(1-methylethyl)-6-phenylpyridin-3-yl)prop-2-ynoic acid 30.3 ml (48.4 mmol) of a 1.6M solution of n-butyllithium in hexane were added dropwise at −70° C. to a solution of 11.5 g (24.2 mmol) of 1,1-dibromo-2-(4-(4-fluorophenyl)-2-(1-methylethyl)-6-phenylpyridin-3-yl)ethane (Example 1a) in 70 ml of THF. The resulting solution was stirred at −70° C. for 1 h and then at room temperature for 1 h and subsequently cooled to −60° C. 10.7 g (242 mmol) of crushed dry ice were added and then the reaction mixture was slowly brought to room temperature, hydrolyzed on ice-water, acidified with dilute hydrochloric acid and extracted several times with ether. The combined organic phases were washed with saturated NaCl solution, dried over MgSO₄ and evaporated. The residue was 11.0 g of the title compound which was reacted further without purification. For analytical purposes, a small amount of the crude product was purified on silica gel (dichloromethane/methanol 9:1).

Melting point: 152°–153° C.; NMR: δ=1.4 (m, 7H), 3.7 (h, J=7 Hz, 1H), 7.2 (m, 2H), 7.4–7.6 (m, 6H), 8.2 (m, 2H). MS m/e=360 (M⁺+H) C₂₃H₁₈FNO₂.

B) Methyl 3-(4-(4-fluorophenyl)-2-(1-methylethyl)-6-phenylpyridin-3-yl)prop-2-ynoate 11.0 g of the crude 3-(4-(4-fluorophenyl)-2-(1-methylethyl)-6-phenylpyridin-3-yl)prop-2-ynoic acid were dissolved in 400 ml of diethyl ether, and ethereal diazomethane solution was added in portions until the reaction was complete according to TLC. The solvent was evaporated off and then the remaining crude ester was purified by column chromatography (silica gel; cyclohexane/dichloromethane 1:1). The title compound was obtained in a yield of 8.85 g, corresponding to 98% based on the dibromide employed.

Melting point: 118°–120° C.; NMR: δ=1.4 (d, J=7 Hz, 6H), 3.7 (h, J=7 Hz, 1H), 3.8 (s, 3H), 7.0–7.8 (m, 8H), 8.2 (m, 2H) MS: m/e=374 (M⁺+H) C₂₄H₂₀FNO₂.

EXAMPLES 2b–2m:

The compounds listed in Table 2 were obtained in analogy to Example 2a

EXAMPLE 3

General procedure for the preparation of compounds of the general formula X

EXAMPLE 3a 3-(4-(4-Fluorophenyl)-2-(1-methylethyl)-6-phenylpyridin-3-yl)prop-2-yn-1-ol (R=a; X=Y—Z=N=C(C₆H₅)—CH, R¹=iC₃H₇, R²=4—FC₆H₄)

49 ml (58.6 mmol) of a 1.2M solution of DIBAH in toluene were added dropwise at 0° C. to a solution of 8.80 g (23.6 mmol) of methyl 3-(4-(4-fluorophenyl)-2-(1-methylethyl)-6-phenylpyridin-3-yl)prop-2-ynoate (Example 2a) in 100 ml of toluene, and the mixture was stirred at 0°–20° C., checking by TLC until reaction was complete (1.5 h). 100 ml of ethyl acetate were added and then the mixture was stirred for a further 30 min and then poured into 100 ml of saturated NaCl solution, acidified with dilute hydrochloric acid until the aluminum salts had dissolved, and extracted by shaking several times with ethyl acetate. The combined organic extracts were washed with saturated NaHCO₃ solution and water, dried over MgSO₄ and evaporated. The residue was purified by chromatography (silica gel; cyclohexane/dichloromethane 1:1). 7.14 g (88%) of the title compound were obtained.

Melting point: 119°–121° C.; NMR: δ=1.4 (d, J=7 Hz, 6H), 1.6 (s, 1H), 3.6 (h, J=7 Hz, 1H), 4.5 (s, 2H), 7.0–7.7 (m, 8H), 8.2 (m, 2H). MS: m/e=346 (M⁺+H) C₂₃H₂₀FNO.

TABLE 2

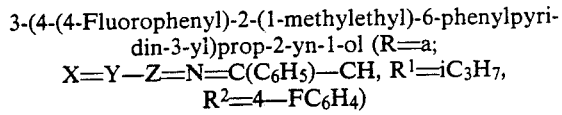

| Example | X | Y | Z | R¹ | R² | R¹⁵ | Yield % | MS: m/e = |
|---------|---|---|---|----|----|-----|---------|-----------|
| 2b | N | 4-FC₆H₄—C | CH | iC₃H₇ | 4-FC₆H₄ | CH₃ | 75 | 391 (M⁺) C₂₄H₁₉F₂NO₂ |
| 2c | N | C₆H₅—C | CH | cC₃H₇ | 4-FC₆H₄ | CH₃ | 78 | 373 (M⁺) C₂₄H₁₈FNO₂ m.p. 144–148° C. |
| 2d | N | C₆H₅—C | N | iC₃H₇ | 4-FC₆H₄ | CH₃ | 51 | 374 (M⁺) C₂₃H₁₉FN₂O₂ |
| 2e | N | 4-FC₆H₄—C | N | iC₃H₇ | 4-FC₆H₄ | CH₃ | 70 | 392 (M⁺) C₂₃H₁₈F₂N₂O₂; m.p. 141° C. |
| 2f | N | iC₃H₇—C | N | iC₃H₇ | 4-FC₆H₄ | CH₃ | 76 | 340 (M⁺) C₂₀H₂₁FN₂O₂ |
| 2g | CH | C₆H₅—C | CH | iC₃H₇ | 4-FC₆H₄ | CH₃ | 83 | 372 (M⁺) C₂₅H₂₁FO₂ |
| 2h | CH | iC₃H₇—C | CH | iC₃H₇ | 4-FC₆H₄ | CH₃ | 71 | 338 (M⁺) C₂₂H₂₃FO₂ |
| 2i | N | N | 4-FC₆H₄—C | iC₃H₇ | 4-FC₆H₄ | CH₃ | 70 | 374 (M⁺) C₂₃H₁₉FN₂O₂ |

| Example | U | V | W | R¹ | R² | R¹⁵ | Yield % | MS: m/e = |
|---------|---|---|---|----|----|-----|---------|-----------|
| 2j | C | C₆H₅—N | C—H | iC₃H₇ | 4-FC₆H₄ | CH₃ | 71 | 361 (M⁺) C₂₃H₂₀FNO₂ |
| 2k | C | iC₃H₇—N | C—H | iC₃H₇ | 4-FC₆H₄ | CH₃ | 70 | 327 (M⁺) C₂₀H₂₂FNO₂ |

| Example | A—B | R¹¹ | R¹² | R¹³ | R¹⁵ | Yield % | MS: m/e = |
|---------|-----|-----|-----|-----|-----|---------|-----------|
| 2l | C≡C | iC₃H₇ | 4-FC₆H₄ | 4-FC₆H₄ | CH₃ | 94 | 340 (M⁺) C₂₁H₁₈F₂O₂ |
| 2m | C≡C | iC₃H₇ | 4-F-3-CH₃C₆H₃ | 4-F-3-CH₃C₆H₃ | CH₃ | 76 | 368 (M⁺) C₂₃H₂₂F₂O₂ |

EXAMPLES 3b–3m

The compounds listed in Table 3 were obtained in analogy to Example 3a.

yn1-ol (Example 3 a) and 6.68 g (31.0 mmol) of pyridinium chlorochromate in 150 ml of dichloromethane was stirred at room temperature. The progress of the reaction was checked by TLC. All the starting material had reacted after 3 h. The reaction solution was filtered through a layer of silica gel and evaporated. Column chromatography of the residue (silica gel; cyclohexane/ethyl acetate 20:1) provided 6.4 g (90%) of the title compound.

NMR: δ=1.4 (d, J=7 Hz, 6H), 3.8 (h, J=7 Hz, 1H), 7.2 (m, 2H), 7.4–7.6 (m, 6H), 8.2 (m, 2H), 9.7 (s, 1H). MS: m/e=344 (M++H) $C_{23}H_{18}FNO$.

TABLE 3

$$R = \underset{X=Y}{\overset{R^1}{\underset{\phantom{X}}{\diagdown}}} \overset{R^2}{\underset{Z}{\diagup}} \qquad R\!-\!\!\equiv\!\!-CH_2OH$$

| Example | X | Y | Z | $R^1$ | $R^2$ | Yield % | MS: m/e = |
|---|---|---|---|---|---|---|---|
| 3b | N | 4-FC$_6$H$_4$—C | CH | iC$_3$H$_7$ | 4-FC$_6$H$_4$ | 94 | 363 (M$^+$) C$_{23}$H$_{19}$F$_2$NO |
| 3c | N | C$_6$H$_5$—C | CH | cC$_3$H$_7$ | 4-FC$_6$H$_4$ | 97 | 345 (M$^+$) C$_{23}$H$_{18}$FNO; m.p. 105–109° C. |
| 3d | N | C$_6$H$_5$—C | N | iC$_3$H$_7$ | 4-FC$_6$H$_4$ | 93 | 346 (M$^+$) C$_{22}$H$_{19}$FN$_2$O; m.p. 163° C. |
| 3e | N | 4-FC$_6$H$_4$—C | N | iC$_3$H$_7$ | 4-FC$_6$H$_4$ | 98 | 364 (M$^+$) C$_{22}$H$_{18}$F$_2$N$_2$O$_2$; m.p. 142° C. |
| 3f | N | iC$_3$H$_7$—C | N | iC$_3$H$_7$ | 4-FC$_6$H$_4$ | 91 | 312 (M$^+$) C$_{19}$H$_{21}$FN$_2$O |
| 3g | CH | C$_6$H$_5$—C | CH | iC$_3$H$_7$ | 4-FC$_6$H$_4$ | 95 | 344 (M$^+$) C$_{24}$H$_{21}$FO |
| 3h | CH | iC$_3$H$_7$—C | CH | iC$_3$H$_7$ | 4-FC$_6$H$_4$ | 95 | 310 (M$^+$) C$_{21}$H$_{23}$FO |
| 3i | N | N | 4-FC$_6$H$_4$—C | iC$_3$H$_7$ | 4-FC$_6$H$_4$ | 86 | 346 (M$^+$) C$_{22}$H$_{19}$FN$_2$O |

$$R = \overset{R^6}{\underset{V\!-\!W}{\underset{|}{U}}}\overset{R^7}{\phantom{X}} \qquad R\!-\!\!\equiv\!\!-CH_2OH$$

| Example | U | V | W | $R^6$ | $R^7$ | Yield % | MS: m/e = |
|---|---|---|---|---|---|---|---|
| 3j | C | C$_6$H$_5$—N | C—H | iC$_3$H$_7$ | 4-FC$_6$H$_4$ | 96 | 333 (M$^+$) C$_{22}$H$_{20}$FNO |
| 3k | C | iC$_3$H$_7$—N | C—H | iC$_3$H$_7$ | 4-FC$_6$H$_4$ | 90 | 299 (M$^+$) C$_{19}$H$_{22}$FNO |

$$R\!-\!\!\equiv\!\!-CH_2OH \qquad R = \overset{R^{12}}{\underset{R^{11}}{\underset{|}{A\!-\!B}}}\!\!\diagdown R^{13}$$

| Example | A—B | $R^{11}$ | $R^{12}$ | $R^{13}$ | Yield % | MS: m/e = |
|---|---|---|---|---|---|---|
| 3l | C=C | iC$_3$H$_7$ | 4-FC$_6$H$_4$ | 4-FC$_6$H$_4$ | 74 | 312 (M$^+$) C$_{22}$H$_{16}$F$_2$O |
| 3m | C=C | iC$_3$H$_7$ | 4-F—3-CH$_3$C$_6$H$_3$ | 4-F—3-CH$_3$C$_6$H$_3$ | 81 | 340 (M$^+$) C$_{22}$H$_{22}$F$_2$O |

EXAMPLE 4

General procedure for the preparation of compounds of the general formula III

EXAMPLE 4 a 3-(4-(4-Fluorophenyl)-2-(1-methylethyl)-6-phenylpyridin-3-yl)prop-2-ynal (R=a; X=Y—Z=N=C(C$_6$H$_5$)—CH, R$^1$=iC$_3$H$_7$, R$^2$=4—FC$_6$H$_4$)

A solution of 7.14 g (20.7 mmol) of 3-(4-(4-fluorophenyl)-2-(1-methylethyl)-6-phenylpyridin-3-yl)prop-2-

EXAMPLE 4 b–4 m

The compounds listed in Table 4 were obtained in analogy to Example 4 a.

TABLE 4

$$R = \underset{X=Y}{\overset{R^1}{\underset{\phantom{X}}{\diagdown}}} \overset{R^2}{\underset{Z}{\diagup}} \qquad R\!-\!\!\equiv\!\!-CHO$$

| Example | X | Y | Z | $R^1$ | $R^2$ | Yield % | MS: m/e = |
|---|---|---|---|---|---|---|---|
| 4b | N | 4-FC$_6$H$_4$—C | CH | iC$_3$H$_7$ | 4-FC$_6$H$_4$ | 85 | 361 (M$^+$) C$_{23}$H$_{17}$F$_2$NO |
| 4c | N | C$_6$H$_5$—C | CH | cC$_3$H$_7$ | 4-FC$_6$H$_4$ | 82 | 343 (M$^+$) C$_{23}$H$_{16}$FNO |
| 4d | N | C$_6$H$_5$—C | N | iC$_3$H$_7$ | 4-FC$_6$H$_4$ | 65 | 344 (M$^+$) C$_{22}$H$_{17}$FN$_2$O |
| 4e | N | 4-FC$_6$H$_4$—C | N | iC$_3$H$_7$ | 4-FC$_6$H$_4$ | 70 | 362 (M$^+$) C$_{22}$H$_{16}$F$_2$N$_2$O |
| 4f | N | iC$_3$H$_7$—C | N | iC$_3$H$_7$ | 4-FC$_6$H$_4$ | 75 | 310 (M$^+$) C$_{19}$H$_{19}$FN$_2$O |
| 4g | CH | C$_6$H$_5$—C | CH | iC$_3$H$_7$ | 4-FC$_6$H$_4$ | 89 | 342 (M$^+$) C$_{24}$H$_{19}$FO |
| 4h | CH | iC$_3$H$_7$—C | CH | iC$_3$H$_7$ | 4-FC$_6$H$_4$ | 95 | 308 (M$^+$) C$_{21}$H$_{21}$FO |
| 4i | N | N | 4-FC$_6$H$_4$—C | iC$_3$H$_7$ | 4-FC$_6$H$_4$ | 60 | 344 (M$^+$) C$_{22}$H$_{17}$FN$_2$O |

TABLE 4-continued

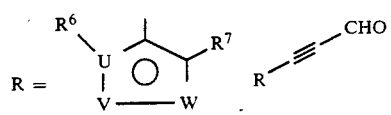

| Example | U | V | W | R$^6$ | R$^7$ | Yield % | MS: m/e = |
|---|---|---|---|---|---|---|---|
| 4j | C | C$_6$H$_5$—N | C—H | iC$_3$H$_7$ | 4-FC$_6$H$_4$ | 88 | 331 (M$^+$) C$_{22}$H$_{18}$NO |
| 4k | C | iC$_3$H$_7$—N | C—H | iC$_3$H$_7$ | 4-FC$_6$H$_4$ | 77 | 297 (M$^+$) C$_{19}$H$_{20}$FNO |

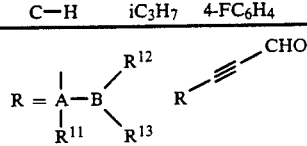

| Example | A—B | R$^{11}$ | R$^{12}$ | R$^{13}$ | Yield % | MS: m/e = |
|---|---|---|---|---|---|---|
| 4l | C=C | iC$_3$H$_7$ | 4-FC$_6$H$_4$ | 4-FC$_6$H$_4$ | 70 | 318 (M$^+$) C$_{20}$H$_{16}$F$_2$O |
| 4m | C=C | iC$_3$H$_7$ | 4-F-3-CH$_3$C$_6$H$_3$ | 4-F-3-CH$_3$C$_6$H$_3$ | 73 | 338 (M$^+$) C$_{22}$H$_{20}$F$_2$O |

EXAMPLE 5

General procedure for the preparation of compounds of the general formula IV

EXAMPLE 5 a

Methyl 7-(4-(4-fluorophenyl)-2-(1-methylethyl)-6-phenylpyrig (9.0 mmol) of 3-(4-(4-fluorophenyl)-2-(1-methylethyl)-6-phenylpyridin-3-yl)prop-2-ynal (Example 4 a) in 30 ml of THF was added dropwise. The reaction mixture was stirred at −78° C. for 2 h, acidified with 1M hydrochloric acid and extracted several times with ether. The combined organic phases were washed with NaHCO$_3$ solution and water, dried over magnesium sulfate and evaporated. Purification of the residue by TABLE 5-continued $$R = \begin{matrix} R^{12} \\ | \\ A-B \\ | \\ R^{11} \end{matrix} R^{13}$$

[Product structure: R–C≡C–CH(OH)–CH₂–C(=O)–CH₂–CO₂R⁰]

| Example | A—B | R¹¹ | R¹² | R¹³ | R⁰ | Yield % | MS: m/e = |
|---------|-----|-----|-----|-----|-----|---------|-----------|
| 5l | C≡C | iC₃H₇ | 4-FC₆H₄ | 4-FC₆H₄ | CH₃ | 75 | 426 (M⁺) C₂₅H₂₄F₂O₄ |
| 5m | C≡C | iC₃H₇ | 4-F-3-CH₃C₆H₃ | 4-F-3-CH₃C₆H₃ | CH₃ | 61 | 454 (M⁺) C₂₇H₂₈F₂O₄ |

EXAMPLE 6

General procedure for the preparation of compounds of the general formula I

EXAMPLE 6 a

Methyl 3RS, 5SR-dihydroxy-7-(4-(4-fluorophenyl)-2-(1-methylethyl)-6-phenylpyridin-3-yl)hept-6-ynoate (R=a; X=Y—Z=N=C(C₆H₅)—CH, R¹=iC₃H₇, R²=4—FC₆H₄, R⁰=CH₃)

6.75 ml of a 1M solution of triethylborane in THF were diluted with 40 ml of THF and, at 0° C., 10 ml of methanol were added dropwise. The resulting solution was stirred at 0° C. for 1 h and cooled to −78° C. A solution of 2.07 g (4.5 mmol) of the keto ester (from Example 5a) in a little THF was added dropwise and then the mixture was stirred at −78° C. for 30 min. Subsequently 340 mg (9.0 mmol) of sodium borohydride were added and the resulting mixture was stirred further at −78° C. for 3 h. For the working up, the reaction mixture was diluted with ethyl acetate, poured onto saturated ammonium chloride solution and extracted several times with ethyl acetate. The organic phases were dried (MgSO₄) and concentrated and, to remove boric esters, the residue was taken up in methanol and evaporated 3×each. The remaining crude product was purified by column chromatography (cyclohexane/ethyl acetate 4:1). The yield of pure title compound was 1.45 g (70%).

Melting point: 134° C.; NMR: δ = 1.4(d, J = 7 Hz, 6H), 1.8(m, 1H), 2.0(m, 1H), 2.4–2.6 (m, 3H), 2.7(d, J = 3 Hz, 1H), 3.4(d, J = 2 Hz, 1H), 3.4(s, 3H), 4.2(m, 1H), 5.3(m, 1H), 7.2(m, 2H), 7.4–7.6(m, 6H), 8.1(m, 2H). MS: m/e = 462 (M⁺ + H) C₂₈H₂₈FNO₄.

EXAMPLES 6 b–6 m

The compounds listed in Table 6 were obtained in analogy to Examples 6a.

TABLE 6

[Starting material structure with R¹, R², X, Y, Z] → [Product: R–C≡C–CH(OH)–CH₂–CH(OH)–CH₂–CO₂R⁰]

| Example | X | Y | Z | R¹ | R² | R⁰ | Yield % | ¹H NMR: δ/ppm; MS: m/e |
|---------|---|---|---|-----|-----|-----|---------|-------------------------|
| 6b | N | 4-FC₆H₄—C | CH | iC₃H₇ | 4-FC₆H₄ | CH₃ | 77 | 1.4(d, J=7Hz, 6H), 1.8(m, 1H), 2.0(m, 1H), 2.5(m, 2H), 2.7(s, 1H), 3.4(s, 1H), 3.8(s, 3H), 4.1(h, J=7Hz, 1H), 4.2(m, 1H), 4.8(m, 1H), 7.1–8.1(m, 9H). 479(M⁺)C₂₈H₂₇F₂NO₄ |
| 6c | N | C₆H₅—C | CH | cC₃H₇ | 4-FC₆H₄ | CH₃ | 80 | 1.1(m, 2H), 1.3(m, 2H), 1.8(m, 1H)2.0 (m, 1H), 2.5–2.7(m, 2H), 2.8(d, J= 4Hz, 1H), 3.4(d, J=3Hz, 1H), 3.7(s, 3H), 4.2(m, 1H), 4.9(m, 1H), 7.1(m, 2H), 7.3–7.6(m, 6H), 8.0(m, 2H). 461(M⁺)C₂₈H₂₆FNO₄; m.p. 96–100° C. |
| 6d | N | C₆H₅—C | N | iC₃H₇ | 4-FC₆H₄ | CH₃ | 74 | 1.5(d, J=Hz, 6H), 1.8(m, 1H), 2.0(m, 1H) 2.6(m, 2H), 2.7(s, 1H), 3.4(s, 1H), 3.7 (s, 3H), 4.0(h, J=7Hz, 1H), 4.2(m, 1H), 4.8(m, 1H), 7.2(m, 2H), 7.4–7.8(m, 5H), 8.6(m, 2H). 462(M⁺)C₂₇H₂₇FN₂O₄ |
| 6e | N | 4-FC₆H₄—C | N | iC₃H₇ | 4-FC₆H₄ | CH₃ | 66 | 1.4(d, J=7Hz, 6H), 1.8(m, 1H), 2.0(m, 1H) 2.5(m, 2H), 3.0(s, 1H), 3.5(s, 1H), 3.7(s, 3H), 3.7(h, J=7Hz, 1H), 4.2(m, 1H), 4.9 (m, 1H), 7.1(m, 4H), 8.1(m, 2H) 8.6(m, 2H). 480(M⁺)C₂₇H₂₆F₂N₂O₄; m.p. 73–77° C. |
| 6f | N | iC₃H₇—C | N | iC₃H₇ | 4-FC₆H₄ | CH₃ | 61 | 1.3(d, J=7Hz, 6H), 1.5(d, 7Hz, 6H), 1.8 (m, 1H), 2.0(m, 1H), 2.6(m, 2H), 2.7(s, 1H), 3.4(s, 1H), 3.5(h, J=7Hz, 1H), 3.7 (s, 3H), 4.0(h, J=7Hz, 1H), 4.2(m, 1H), 4.8(m, 1H), 7.1(m, 2H), 7.6(m, 2H). 428(M⁺)C₂₄H₂₉FN₂O₄ |
| 6g | CH | C₆H₅—C | CH | iC₃H₇ | 4-FC₆H₄ | CH₃ | 79 | 1.3(d, J=7Hz, 6H), 1.8(m, 1H), 2.0(m, 1H) 2.5(m, 2H), 2.7(s, 1H), 3.4(s, 1H), 3.7 (s, 3H), 3.9(h, J=7Hz, 1H), 4.2(m, 1H), 4.8 (m, 1H)7.1(m, 2H), 7.4–7.7(m, 9H). |

TABLE 6-continued

| | | | | | | | | |
|---|---|---|---|---|---|---|---|---|
| 6h | CH | iC$_3$H$_7$—C | CH | iC$_3$H$_7$ | 4-FC$_6$H$_4$ | CH$_3$ | 72 | 460(M$^+$)C$_{29}$H$_{29}$FO$_4$ 1.1–1.2(m, 12H), 1.8(m, 1H), 2.0(m, 1H), 2.5(m, 2H), 2.7(s, 1H), 3.4(m, 2H), 3.7(s, 3H) 3.9(h, J=7Hz, 1H), 4.2(m, 1H), 4.8(m, 1H), 7.0–7.4(m, 6H). |
| 6i | N | N | 4-FC$_6$H$_4$—C | iC$_3$H$_7$ | 4-FC$_6$H$_4$ | CH$_3$ | 53 | 426(M$^+$)C$_{26}$H$_{31}$FO$_4$ 1.5(d, J=7Hz, 6H), 1.8(m, 1H), 2.0(m, 1H), 2.5(m, 2H), 2.7(s, 1H), 3.4(s, 1H), 3.7(s, 3H) 3.8(h, J=7Hz, 1H), 4.3(m, 1H), 4.8(m, 1H), 6.9–7.5(m, 8H). 462(M$^+$)C$_{27}$H$_{26}$FN$_2$O$_4$ |

$$R = \begin{array}{c} R^6\diagdown U\diagup\overset{|}{\phantom{O}}\diagdown R^7 \\ V\text{---}W \end{array} \qquad R\diagdown\equiv\diagdown\overset{OH}{\diagup}\diagdown\overset{OH}{\diagup}\diagdown CO_2R^0$$

$^1$H NMR: δ/ppm

| Example | U | V | W | R$^6$ | R$^7$ | R$^0$ | Yield % | MS: m/e |
|---|---|---|---|---|---|---|---|---|
| 6j | C | C$_6$H$_5$—N | C—H | iC$_3$H$_7$ | 4-FC$_6$H$_4$ | CH$_3$ | 73 | 1.3(d, J=7Hz, 6H), 1.8(m, 1H) 2.0(m, 1H), 2.5(m, 2H), 2.7(s, 1H), 3.4(s, 1H), 3.6(h, J=7Hz, 1H), 3.7(s, 3H), 4.2(m, 1H), 4.8(m, 1H), 6.6(s, 1H), 6.8–7.2(m, 7H), 7.5(m, 2H). 449(M$^+$)C$_{27}$H$_{28}$FNO$_4$ |
| 6k | C | iC$_3$H$_7$—N | C—H | iC$_3$H$_7$ | 4-FC$_6$H$_4$ | CH$_3$ | 65 | 1.4(d, J=7Hz, 6H), 1.5(d, J=7Hz 6H), 1.8(m, 1H), 2.0(m, 1H), 2.5(m, 2H), 2.8(s, 1H), 3.5(h, J=7Hz, 1H), 3.7(s, 3H), 4.2(m, 1H), 4.5(h, J=7Hz, 1H), 4.8(m, 1H), 6.6(s, 1H), 7.0(m, 2H), 7.4(m, 2H). 415(M$^+$)C$_{24}$H$_{30}$FNO$_4$ |

$$R = \begin{array}{c} \overset{|}{A}\text{---}\overset{|}{B}\diagdown R^{12} \\ R^{11}\phantom{xxx}R^{13} \end{array} \qquad R\diagdown\equiv\diagdown\overset{OH}{\diagup}\diagdown\overset{OH}{\diagup}\diagdown CO_2R^0$$

$^1$H NMR: δ/ppm

| Example | A—B | R$^{11}$ | R$^{12}$ | R$^{13}$ | R$^0$ | Yield % | MS: m/e |
|---|---|---|---|---|---|---|---|
| 6l | C=C | iC$_3$H$_7$ | 4-FC$_6$H$_4$ | 4-FC$_6$H$_4$ | CH$_3$ | 67 | 1.1(d, J=7Hz, 6H), 1.7(m, 1H), 1.9(m, 1H), 2.4–2.5(m, 2H), 2.6(d, J=3Hz, 1H), 2.7(h, J=7Hz, 1H), 3.4(d, J=3Hz, 1H), 3.7(s, 3H), 4.2(m, 1H), 4.7(m, 1H), 6.9–7.1(m, 6H), 7.3(m, 2H). 428(M$^+$)C$_{25}$H$_{26}$F$_2$O$_4$ |
| 6m | C=C | iC$_3$H$_7$ | 4-F-3-CH$_3$C$_6$H$_3$ | 4-F-3-CH$_3$C$_6$H$_3$ | CH$_3$ | 58 | 1.1(d, J=7Hz, 6H), 1.7(m, 1H), 1.9(m, 1H)2.2–2.5(m, 8H), 2.6(d, J=4Hz 1H), 2.7(h, J=7Hz, 1H)3.5(d, J=4Hz, 1H), 3.7(s, 3H), 4.2(m, 1H), 4.7(m, 1H), 6.9–7.1(m, 6H). 456(M$^+$)C$_{27}$H$_{30}$F$_2$O$_4$ |

1.40 g (3.02 mmol) of methyl 3RS, 5SR-dihydroxy-7-(4-(4-fluorophenyl)-2-(1-methylethyl)-6-phenylpyridin-3-yl)hept-6-ynoate (Example 6 a) were dissolved in 40 ml of abs. ethanol, and 3 ml (30 mmol) of 1M sodium hydroxide solution were added. The reaction solution was stirred at room temperature, checking by TLC. Starting material was no longer detectable after 2 h. The solvent was evaporated off and toluene was added to the solid residue and again evaporated. The residue after drying under high vacuum was 1.47 g (100%) of the title compound in the form of white crystals.

$^1$H NMR(D$_2$O): 1.1(d, J=7 Hz, 6H), 1.6(m, 1H), 1.8(m, 1H), 2.1(dd, J=15 Hz, 9 Hz, 1H), 2.3(dd, J=15 Hz, 3 Hz, 1H), 3.4(h, J=7 Hz, 1H), 3.9(m, 1H), 4.4(dd, J=6 Hz, 6 Hz, 1H), 6.5(s, 1H), 6.7–6.9(m, 7H), 7.3(m, 2H).

EXAMPLES 7b–7m

The compounds listed in Table 7 were obtained in analogy to Example 7a

TABLE 7

$$R = \begin{array}{c} R^1\diagdown\phantom{x}\diagup R^2 \\ X\diagdown\overset{}{Y}\diagup Z \end{array} \qquad R\diagdown\equiv\diagdown\overset{OH}{\diagup}\diagdown\overset{OH}{\diagup}\diagdown CO_2R^0$$

| Example | X | Y | Z | R$^1$ | R$^2$ | R$^0$ | Yield % |
|---|---|---|---|---|---|---|---|
| 7b | N | 4-FC$_6$H$_4$—C | CH | iC$_3$H$_7$ | 4-FC$_6$H$_4$ | Na | 98 |
| 7c | N | C$_6$H$_5$—C | CH | cC$_3$H$_7$ | 4-FC$_6$H$_4$ | Na | 95 |
| 7d | N | C$_6$H$_5$—C | N | iC$_3$H$_7$ | 4-FC$_6$H$_4$ | Na | 99 |
| 7e | N | 4-FC$_6$H$_4$—C | N | iC$_3$H$_7$ | 4-FC$_6$H$_4$ | Na | 99 |
| 7f | N | iC$_3$H$_7$—C | N | iC$_3$H$_7$ | 4-FC$_6$H$_4$ | Na | 91 |
| 7g | CH | C$_6$H$_5$—C | CH | iC$_3$H$_7$ | 4-FC$_6$H$_4$ | Na | 95 |
| 7h | CH | iC$_3$H$_7$—C | CH | iC$_3$H$_7$ | 4-FC$_6$H$_4$ | Na | 98 |

TABLE 7-continued

| | | | | | | |
|---|---|---|---|---|---|---|
| 7i | N | N | | $4\text{-}FC_6H_4\text{—}C$ | $iC_3H_7$ | $4\text{-}FC_6H_4$ | Na | 96 |

$$R = \begin{array}{c} R^6 \\ | \\ U \\ | \\ V \end{array}\begin{array}{c} \\ \\ O \\ \\ W \end{array} R^7 \qquad R\text{—}\equiv\text{—}\overset{OH}{\wedge}\overset{OH}{\wedge}CO_2R^0$$

| Example | U | V | W | $R^6$ | $R^7$ | $R^0$ | Yield % |
|---------|---|---|---|-------|-------|-------|---------|
| 7j | C | $C_6H_5\text{—}N$ | C—H | $iC_3H_7$ | $4\text{-}FC_6H_4$ | Na | 91 |
| 7k | C | $iC_3H_7\text{—}N$ | C—H | $iC_3H_7$ | $4\text{-}FC_6H_4$ | Na | 94 |

$$R = \begin{array}{c} | \\ A \\ | \\ R^{11} \end{array}\begin{array}{c} \\ B \\ \end{array}\begin{array}{c} R^{12} \\ \\ R^{13} \end{array} \qquad R\text{—}\equiv\text{—}\overset{OH}{\wedge}\overset{OH}{\wedge}CO_2R^0$$

| Example | A—B | $R^{11}$ | $R^{12}$ | $R^{13}$ | $R^0$ | Yield % |
|---------|-----|----------|----------|----------|-------|---------|
| 7l | C=C | $iC_3H_7$ | $4\text{-}FC_6H_4$ | $4\text{-}FC_6H_4$ | Na | 99 |
| 7m | C=C | $iC_3H_7$ | $4\text{-}F\text{-}3\text{-}CH_3C_6H_3$ | $4\text{-}F\text{-}3\text{-}CH_3C_6H_3$ | Na | 93 |

EXAMPLE 8

General procedure for the preparation of compounds of the general formula II

EXAMPLE 8 a

6RS-2-(4-(4-Fluorophenyl)-2-(1-methylethyl)-6-phenylpyridin-3-yl)ethynyl-4SR-hydroxy-3,4,5,6-tetrahydro-2H-pyran-2-one (R=a; X=Y—Z=N=C($C_6H_5$)—CH, $R^1$=$iC_3H_7$, $R^2$=4—$FC_6H_4$)

3.3 ml (3.3 mmol) of 1M hydrochloric acid were added to a solution of 1.40 g (2.85 mmol) of sodium 3RS, 5SR-dihydroxy-7-(4-(4-fluorophenyl)-2-(1-methylethyl)-6-phenylpyridin-3-yl)hept-6-ynoate (Example 7 a) in 50 ml of water. The resulting suspension was extracted several times with ethyl acetate. The combined organic layers were washed several times with saturated NaCl solution, dried over MgSO₄ and evaporated, and the remaining resin was dried under high vacuum and subsequently taken up in 20 ml of abs. THF and, while cooling in ice, 0.32 g (3.14 mmol) of triethylamine was added. After 10 min, 0.31 g (2.85 mmol) of methyl chloroformate was added dropwise, and the resulting solution was stirred at 0° C. The progress of the reaction was followed by thin-layer chromatography. After 2 h, the mixture was poured onto water and extracted by shaking several times with ether. The combined organic extracts were washed with water and saturated NaCl solution, dried over MgSO₄ and evaporated. Purification of the residue by chromatography (silica gel; cyclohexane/ethyl acetate 2:1) provided 0.95 g (78%) of the title compound.

Melting point: 161° C.; ¹H NMR: 1.4(d, J=7 Hz, 6H), 1.9(s, 1H), 2.1(m, 2H), 2.5(dd, J=18 Hz, 6 Hz, 1H), 2.7(dd, J=18 Hz, 6 Hz, 1H), 3.7(h, J=7 Hz, 1H), 4.3(m, 1H), 5.5(dd, J=6 Hz, 5 Hz, 1H), 7.2(m, 2H), 7.4–7.6(m, 6H), 8.1(m, 2H). MS: m/e=430 (M+ +H) $C_{27}H_{24}FNO_3$.

EXAMPLES 8 b–8 m

The compounds listed in Table 8 were obtained in analogy to Example 8a.

TABLE 8

$$R = \begin{array}{c} R^1 \\ \diagup \\ X \end{array}\begin{array}{c} | \\ \\ Y \end{array}\begin{array}{c} R^2 \\ \diagdown \\ Z \end{array} \qquad R\text{—}\equiv\text{—}\begin{array}{c} \overset{OH}{\wedge} \\ \diagdown \\ O \end{array}\text{=}O$$

| Example | X | Y | Z | $R^1$ | $R^2$ | Yield % | ¹H NMR: δ/ppm MS: m/e |
|---------|---|---|---|-------|-------|---------|------------------------|
| 8b | N | $4\text{-}FC_6H_4\text{—}C$ | CH | $iC_3H_7$ | $4\text{-}FC_6H_4$ | 75 | 1.4(d, J=7Hz, 6H), 1.9(s, 1H), 2.1 (m, 2H), 2.6(m, 1H), 2.7(m, 1H), 3.8 (h, J=7Hz, 1H), 4.3(m, 1H), 5.5 (dd, J=6Hz, 5Hz, 1H), 7.0–8.1(m, 9H). 447(M+)$C_{27}H_{23}F_2NO_3$ |
| 8c | N | $C_6H_5\text{—}C$ | CH | $cC_3H_7$ | $4\text{-}FC_6H_4$ | 71 | 1.1(m, 2H), 1.3(m, 2H), 2.0(s, 1H) 2.2(m, 2H), 2.5–2.8(m, 3H), 4.3(m 1H), 5.5(dd, J=6Hz, 5Hz, 1H), 7.2 (m, 2H), 7.4–7.6(m, 6H), 8.0(m, 2H). 429(M+)$C_{27}H_{22}FNO_3$; m.p. 152–157° C. |
| 8d | N | $C_6H_5\text{—}C$ | N | $iC_3H_7$ | $4\text{-}FC_6H_4$ | 74 | 1.5(d, J=7Hz, 6H), 2.0(s, 1H), 2.1 (m, 2H), 2.6(m, 1H), 2.8(m, 1H), 3.7(h, J=7Hz, 1H), 4.3(m, 1H), 5.6(dd, J=5Hz, 6Hz, 1H), 7.2(m, 2H), 7.4–7.8(m, 5H), 8.6(m, 2H). 430(M+)$C_{26}H_{23}FN_2O_3$ |
| 8e | N | $4\text{-}FC_6H_4\text{—}C$ | N | $iC_3H_7$ | $4\text{-}FC_6H_4$ | 74 | 1.4(d, J=7Hz, 6H), 2.0(s, 1H), 2.1 (m, 2H), 2.6(m, 1H), 2.8(m, 1H), 3.6 |

TABLE 8-continued

| | | | | | | | ¹H NMR: δ/ppm MS: m/e |
|---|---|---|---|---|---|---|---|
| | | | | | | | (h, J=7Hz, 1H), 4.1(m, 1H), 5.6(dd, J=5Hz, 6Hz, 1H), 7.1(m, 4H), 8.0(m, 2H), 8.6(m, 2H). 448(M⁺)C₂₆H₂₂F₂N₂O₃; m.p. 174-180° C. |
| 8f | N | iC₃H₇—C | N | iC₃H₇ | 4-FC₆H₄ | 68 | 1.3(d, J=7Hz, 6H), 1.5(d, J=7Hz, 6H), 1.8(s, 1H), 2.1(m, 2H), 2.6 (m, 1H), 2.8(m, 1H), 3.5(h, J=7Hz, 1H), 3.6(h, J=7Hz, 1H), 4.3(m, 1H), 5.5(dd, J=6Hz, 5Hz, 1H), 7.2(m, 2H) 7.6(m, 2H). 396(M⁺)C₂₃H₂₅FN₂O₃ |
| 8g | CH | C₆H₅—C | CH | iC₃H₇ | 4-FC₆H₄ | 80 | 1.3(d, J=7Hz, 6H), 1.8(s, 1H), 2.1 (m, 2H), 2.5(m, 1H), 2.7(m, 1H), 3.6(h, J=7Hz, 1H), 4.3(m, 1H), 5.5(dd, J=6Hz, 5Hz, 1H), 7.1(m, 2H), 7.3-7.5(m, 7H), 7.6(m, 2H) 428(M⁺)C₂₈H₂₅FO₃ |
| 8h | CH | iC₃H₇ | CH | iC₃H₇ | 4-FC₆H₄ | 77 | 1.1-1.2(m, 12H), 1.8(s, 1H), 2.1 (m, 2H), 2.5(m, 1H), 2.7(m, 1H), 3.1 (h, J=7Hz, 1H), 3.6(h, J=7Hz, 1H), 4.2(m, 1H), 5.4(dd, J=6Hz, 5Hz, 1H), 7.0-7.4(m, 6H). 394(M⁺)C₂₅H₂₇FO₃ |
| 8i | N | N | 4-FC₆H₄—C | iC₃H₇ | 4-FC₆H₄ | 59 | 1.4(d, J=7Hz, 6H), 1.8(s, 1H), 2.1(m, 2H), 2.5(m, 1H), 2.8(m, 1H) 3.8(h, J=7Hz, 1H), 4.3(m, 1H), 5.5 (dd, J=6Hz, 5Hz, 1H), 7.1-7.5(m, 8H). 448(M⁺)C₂₆H₂₂F₂N₂O₃ |

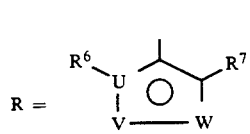 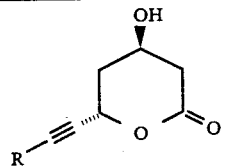

| Example | U | V | W | R⁶ | R⁷ | Yield % | ¹H NMR: δ/ppm MS: m/e |
|---|---|---|---|---|---|---|---|
| 8j | C | C₆H₅—N | C—H | iC₃H₇ | 4-FC₆H₄ | 74 | 1.3(d, J=7Hz, 6H), 1.8(s, 1H), 2.0 (m, 2H), 2.2(m, 1H), 2.4(m, 1H), 3.3 (h, J=7Hz, 1H), 4.2(m, 1H), 5.3(dd, J=6Hz, 5Hz, 1H), 6.6(s, 1H), 6.8-7.2 (m, 7H), 7.5(m, 2H). 417(M⁺)C₂₆H₂₄FNO₃ |
| 8k | C | iC₃H₇—N | C—H | iC₃H₇ | 4-FC₆H₄ | 69 | 1.4(d, J=7Hz, 6H), 1.5(d, J=Hz, 6H), 1.9(s, 1H), 2.1(m, 2H), 2.5(m, 1H), 2.7(m, 1H), 3.5(h, J=7Hz, 1H), 4.3 (m, 1H), 4.5(h, J=7Hz, 1H), 5.5(dd, J=6Hz, 5Hz, 1H), 6.6(s, 1H), 7.1(m 2H), 7.3(m, 2H). 383(M⁺)C₂₃H₂₆FNO₃ |

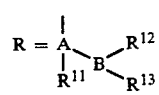 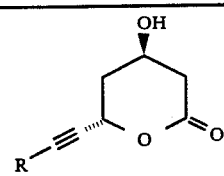

| Example | A—B | R¹¹ | R¹² | R¹³ | Yield % | ¹H NMR: δ/ppm MS: m/e |
|---|---|---|---|---|---|---|
| 8l | C═C | iC₃H₇ | 4-FC₆H₄ | 4-FC₆H₄ | 81 | 1.1(d, J=7Hz, 6H), 1.9(s, 1H), 2.1(m, 2H), 2.4-2.8(m, 3H), 4.2(m, 1H), 5.3(dd, J=6Hz, 5Hz, 1H), 6.9-7.1(m, 8H). 396(M⁺)C₂₄H₂₂F₂O₃ |
| 8m | C═C | iC₃H₇ | 4-F-3-CH₃C₆H₃ | 4-F-3-CH₃C₆H₃ | 75 | 1.1(d, J=7Hz, 6H), 1.9(s, 1H), 2.0-2.3(m, 8H), 2.4-2.8(m, 3H), 4.2(m, 1H), 5.3(dd, J=6Hz, 5Hz, 1H), 6.9-7.1 (m, 6H). 424(m⁺)C₂₆H₂₆F₂O₃ |

We claim:
1. A compound of the formula I

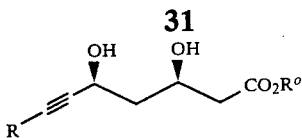

I or a corresponding lactone of the formula II

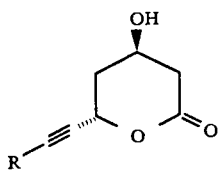

II where, in formulae I and II, R is a radical of formula a

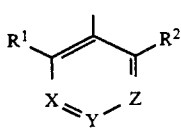

a in which

R$^1$ and R$^2$ are, independently of one another, a straight-chain or branched alkyl or alkenyl radical having up to 6 carbon atoms, a saturated or up to doubly unsaturated cyclic hydrocarbon radical having 3-6 carbon atoms or a phenyl radical which is optionally substituted by 1-3 identical or different radicals selected from the group consisting of straight-chain or branched alkyl having up to 4 carbon atoms, halogen, alkoxy having up to 4 carbon atoms and hydroxyl, and X=Y—Z is a group of the formula N=CR$^4$—CR$^5$, in which R$^4$ and R$^5$ are, independently of one another, hydrogen, a straight-chain or branched alkyl or alkenyl radical having up to 6 carbon atoms, a saturated or up to doubly unsaturated cyclic hydrocarbon radical having 3-6 carbon atoms or a phenyl radical which is optionally substituted by 1-3 identical or different radicals selected from the group consisting of straight-chain or branched alkyl having up to 4 carbon atoms, halogen, alkoxy having up to 4 carbon atoms and hydroxyl, and R$^0$ is hydrogen, a straight-chain or branched alkyl radical having up to 6 carbon atoms, alkali metal or ammonium, or a physiologically tolerated salt thereof.

2. The compound as claimed in claim 1, wherein R is a radical of the formula a in which R$^1$ is a straight-chain or branched alkyl radical having up to 4 carbon atoms or a cycloalkyl radical having 3-6 carbon atoms, R$^2$ is a phenyl radical which is optionally substituted by 1-3 identical or different radicals selected from the group consisting of C$_1$-C$_4$-alkyl, fluorine, chlorine, alkoxy having 1-4 carbon atoms and hydroxyl, and X=Y—Z is of the formula N=CR$^4$—CR$^5$, in which R$^4$ is a straight-chain or branched alkyl radical having up to 4 carbon atoms, a cycloalkyl radical having 3-6 carbon atoms, or a phenyl radical which is optionally substituted by 1-3 identical or different radicals selected from the group consisting of C$_1$-C$_4$-alkyl, fluorine, chlorine, alkoxy having 1-4 carbon atoms and hydroxyl, R$^5$ is hydrogen, a straight-chain or branched alkyl radical having up to 4 carbon atoms, a cycloalkyl radical having 3-6 carbon atoms or a phenyl radical which is optionally substituted by 1-3 identical or different radicals selected from the group consisting of C$_1$-C$_4$-alkyl, fluorine, chlorine, alkoxy having 1-4 carbon atoms and hydroxyl, and R$^0$ is hydrogen, a straight-chain or branched alkyl radical having up to 4 carbon atoms, sodium, or potassium.

3. The compound as claimed in claim 1, wherein R is a radical of the formula a in which X=Y—Z is a group of the formula N=CR$^4$—CR$^5$ in which R$^4$ is isopropyl, tert.-butyl, phenyl or 4-fluorophenyl and R$^5$ is hydrogen, and R$^1$ is isopropyl or cyclopropyl and R$^2$ is 4-fluorophenyl, and R$^0$ is hydrogen, methyl, ethyl, tert.-butyl, sodium or potassium.

4. The compound as claimed in claim 1, which has a structural formula of the formula I.

5. The compound as claimed in claim 1, which has a structural formula of the formula II.

6. A pharmaceutical composition for the prophylaxis and treatment of hypercholesterolemia comprising an amount effective for use in the therapy of a mammal of a compound as claimed in claim 10 or a physiologically tolerated salt thereof, together with a pharmaceutically acceptable carrier.

7. A method for the prophylaxis and treatment of hypercholesterolemia in a mammal which comprises administering to the mammal an effective amount of a compound as claimed in claim 1 or a physiologically tolerated salt thereof.

8. A method for the prophylaxis and treatment of hypercholesterolemia in a mammal which comprises administering to the mammal a pharmaceutical composition as claimed in claim 6.

* * * * *

UNITED STATES PATENT AND TRADEMARK OFFICE
CERTIFICATE OF CORRECTION

PATENT NO. : 5,091,386
DATED : February 25, 1992
INVENTOR(S) : Kurt Kesseler et al.

It is certified that error appears in the above-identified patent and that said Letters Patent is hereby corrected as shown below:

Title page, item [75], before "Soden" insert --Bad--.

Title page, item [73], change "Frankfurt" to --Frankfurt am Main--.

Claim 6, column 32, line 46, change "claim 10, to --claim 1--.

Signed and Sealed this

Twenty-first Day of September, 1993

Attest:

BRUCE LEHMAN

*Attesting Officer*           *Commissioner of Patents and Trademarks*